United States Patent
Glocker et al.

(10) Patent No.: US 8,712,186 B2
(45) Date of Patent: Apr. 29, 2014

(54) METHOD FOR COMBINING IMAGES AND MAGNETIC RESONANCE SCANNER

(75) Inventors: Benjamin Glocker, Munich (DE); Nassir Navab, Munich (DE); Christian Wachinger, Munich (DE); Jochen Zeltner, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1211 days.

(21) Appl. No.: 12/461,993

(22) Filed: Aug. 31, 2009

(65) Prior Publication Data

US 2010/0067762 A1    Mar. 18, 2010

(30) Foreign Application Priority Data

Sep. 1, 2008 (DE) .......................... 10 2008 045 278

(51) Int. Cl.
 *G06K 9/36* (2006.01)
 *G06K 9/00* (2006.01)
(52) U.S. Cl.
 USPC ............ 382/284; 382/285; 382/131; 345/629
(58) Field of Classification Search
 USPC ......... 382/128–131, 162, 165, 181, 190, 195, 382/199, 218, 276, 284, 285, 291, 294; 345/629–641, 501
 See application file for complete search history.

(56) References Cited

U.S. PATENT DOCUMENTS

| | | | | |
|---|---|---|---|---|
| 5,764,860 A * | 6/1998 | Yatsuzuka | ...................... | 706/25 |
| 6,097,833 A | 8/2000 | Lobregt et al. | | |
| 6,151,611 A * | 11/2000 | Siegel | ........................... | 715/224 |
| 6,208,758 B1 * | 3/2001 | Ono et al. | ..................... | 382/190 |
| 6,239,834 B1 * | 5/2001 | Miyaji et al. | .................. | 348/193 |
| 6,434,279 B1 * | 8/2002 | Shiba | ........................... | 382/294 |
| 6,638,226 B2 * | 10/2003 | He et al. | ........................ | 600/443 |
| 7,573,491 B2 * | 8/2009 | Hartkop et al. | ............... | 345/672 |
| 7,725,154 B2 * | 5/2010 | Beck et al. | ..................... | 600/407 |

(Continued)

FOREIGN PATENT DOCUMENTS

| | | |
|---|---|---|
| DE | 102006039389 A1 | 2/2008 |
| EP | 0655861 A1 | 5/1995 |
| EP | 1942350 A1 | 7/2008 |
| WO | WO 2006135003 A1 | 12/2006 |

OTHER PUBLICATIONS

Gramoll et al. "Math eBook Monotonic Function" (2006) eCourses "www.ecourses.ou.edu/cgi-bin/ebook.cgi?doc=&topic=ma&chap_sec=04.4&page=theory".*

(Continued)

*Primary Examiner* — Chan Park
*Assistant Examiner* — Mia M Thomas
(74) *Attorney, Agent, or Firm* — Harness, Dickey & Pierce, P.L.C.

(57) ABSTRACT

A method of combining a first image of a first region and a second image of a second region, having an overlapping region therebetween. The method including determining a superposed image as a weighted superposition of the first image and the second image in the overlap region, transforming the first image and the second image on the basis of a comparison of at least one of the first image and the second image with the determined superposed image; determining a further superposed image from the transformed first image and the transformed second image; and generating an overall image from the further superposed image when at least one convergence criterion is satisfied.

25 Claims, 9 Drawing Sheets

(56) References Cited

U.S. PATENT DOCUMENTS

| | | | |
|---|---|---|---|
| 7,787,684 B2 * | 8/2010 | Beck et al. | 382/131 |
| 7,812,603 B2 * | 10/2010 | Ritter | 324/307 |
| 7,857,708 B2 * | 12/2010 | Ueda et al. | 473/257 |
| 8,115,760 B2 * | 2/2012 | Rust | 345/419 |
| 8,199,992 B2 * | 6/2012 | Ritter | 382/131 |
| 8,260,021 B2 * | 9/2012 | Ritter | 382/131 |
| 2003/0044055 A1 * | 3/2003 | Park et al. | 382/130 |
| 2003/0076361 A1 | 4/2003 | Chiba et al. | |
| 2005/0058368 A1 * | 3/2005 | Moriguchi et al. | 382/280 |
| 2006/0285735 A1 * | 12/2006 | Hagen et al. | 382/128 |
| 2006/0293588 A1 * | 12/2006 | Beck et al. | 600/410 |
| 2007/0036413 A1 * | 2/2007 | Beck et al. | 382/128 |
| 2007/0142723 A1 * | 6/2007 | Leach et al. | 600/410 |
| 2007/0230823 A1 * | 10/2007 | Weng et al. | 382/286 |
| 2008/0068012 A1 * | 3/2008 | Werthner | 324/309 |
| 2008/0285833 A1 * | 11/2008 | Fu et al. | 382/131 |
| 2008/0285834 A1 * | 11/2008 | Fu et al. | 382/131 |
| 2009/0030302 A1 | 1/2009 | Ochi et al. | |
| 2009/0210367 A1 * | 8/2009 | Armstrong et al. | 706/13 |
| 2011/0002522 A1 * | 1/2011 | Goto et al. | 382/131 |

OTHER PUBLICATIONS

Ganguly et al. "A Cognitive Study on Medical Imaging" International Journal Bio-Science and Bio-Technology vol. 2, No. 3, Sep. 2010, pp. 1-18.*

Lauenstein T.C. et al: "Whole—Body MR Imaging: Evaluation of Patients for Metastases", Radiology 233(1), 2004, p. 139-148; Others; 2004.

Chang, H; Fitzpatrick, J.: "A Technique for Accurate Magnetic Resonance Imaging in the Presence of Field Inhomogeneities", IEEE TMI 11(3), 1992, p. 319-329; Others; 1992.

Doran, S. et al: "A Complete distortion correction for MR images: I. Gradient warp correction", Physics in Medicine and Biology 50, 2005, p. 1343-1361; Others; 2005.

Reinsberg, S. et al: "A complete distortion correction for MR images: II. Rectification of static-field inhomogebeities by similarity-based profile mapping", Phys. Med. Biol. 50, 2005, p. 2651-2661; Others; 2005.

Goyen, M: "Real Whole Body MRI: Requirements, Indications, Perspectives", McGraw-Hill, Chapter 6, 10, 3, 2007; Others; 2007.

Kannengießer, S.A.R. et al: "Geometric Distortion Correction in Gradient—Echo Imaging by Use of Dynamic Time Warping", Magnetic Resonance in MEdicine 42, p. 585-590, 1999; Others; 1999.

Bhatia, K.K. et al: "Constitent groupwise non-rigid registration for atlas construction." IEEE Biomedical Imaging: Nano to Macro, vol. 1, 2004, Seiten 908-911; Others; 2004.

Glocker, Ben et al: "Effiziente nichtlineare Registrierung mittels diskreter Optimierung. Proc. Bildverarbeitung für die Medizin 2008, 6.-8.04.2008" Seite 87-91; Others; 2008.

* cited by examiner

120
121 — joining region

FIG 14

122
123 — joining region

METHOD FOR COMBINING IMAGES AND MAGNETIC RESONANCE SCANNER

PRIORITY STATEMENT

The present application hereby claims priority under 35 U.S.C. §119 on German patent application number DE 10 2008 045 278.5 filed Sep. 1, 2008 the entire contents of which are hereby incorporated herein by reference.

FIELD

At least one embodiment of the present invention generally relates to a method for combining images, in particular from magnetic resonance records, and/or a magnetic resonance scanner. At least one embodiment of the invention can be utilized in particular for generating whole-body images using magnetic resonance imaging.

BACKGROUND

Imaging using magnetic resonance (MR) imaging has in recent years established itself as a substantial aid for examining objects, particularly in medical diagnostics. These days, even the generation of high-resolution whole-body images for use in medical diagnostics seems to be possible. To this end, MR records, for example, from different regions of an examination object can be generated and combined to form an overall image. Inhomogeneities in the B0 field or spatial variations of magnetic field gradients, for example in the read-out and/or slice direction, can lead to distortions in the MR records, in particular in the edge regions thereof, which make combining the MR records more difficult.

Both the use of MR scanners with a larger field of view (FOV), which are advantageous in terms of the time required to generate an MR record, and the use of MR scanners with shorter magnet designs, which are advantageous in avoiding the patient feeling constricted, can favor inhomogeneities in the B0 field and variations of magnetic field gradients and can make combining different MR records even more difficult.

The paper by Stefan A. Reinsberg et al., "A complete distortion correction for MR images: II. Rectification of static-field inhomogeneities by similarity-based profile mapping", Phys. Med. Biol. 50 (2005), pp. 2651-2661 and EP 1 942 350 A1 propose decreasing distortions in MR records by recording two MR records of the same region of an examination object, with the polarity of the read-out gradient being reversed in the two MR records, and elastically registering one of the MR records against the other MR record. However, this method leads to increased expenditure of time since two MR records of the same region of an examination object have to be generated with differing polarity of the read-out gradient. Moreover, the registration is effected against an MR record as a reference image which can in turn be distorted itself.

SUMMARY

In at least one embodiment, the invention includes specifying an improved method for combining images of an examination object and an improved magnetic resonance scanner. In particular, a method and a magnetic resonance scanner are disclosed which do not require the generation of a number of MR records of each region of the examination object to be combined into an overall image.

According to at least one embodiment of the invention, a method for combining a first image and a second image of an examination object is specified, with the first and the second image having an overlap region. A superposed image is determined as a superposition of the first image and the second image, weighted in the overlap region in accordance with a weighting function, with the weighting function representing a weight of the first image and/or of the second image at positions of the superposed image and varying spatially in the overlap region. The first and the second image are then transformed on the basis of a comparison of the first image and/or of the second image with the superposed image.

Since the superposed image of the first and the second image obtained by the method is used as a reference image for the transformation of the first and the second image, it is not necessary to generate a reference from an additional record, e.g. an MR record with magnetic field gradients of opposite polarity, for the transformation of the images. Use of the spatially variable weighting function affords the possibility of taking into account information regarding the image quality when determining the superposed image, in particular regarding the spatial variation and the occurrence of distortions in particular image regions.

The first image and the second image can show regions of the examination object which are adjacent to each another along an axis, wherein the weighting function is variable in the overlap region along the axis; said function, for example, possibly being a substantially linear function of a coordinate along the axis. This affords the possibility of taking into account the fact that, in the case of an MR record, the regions in a neighborhood of the axial edges of the MR record typically have a greater distortion than regions in a neighborhood of the magnetic isocenter and therefore should be weighted less strongly in the superposed image used as the reference image. In general, the weighting function can be selected such that a weighting of pixels of the first image decreases in the overlap region in the direction of an edge of the first image, and that a weighting of pixels of the second image decreases in the overlap region in the direction of an edge of the second image. Advantageously, the weighting function is a monotonic function of a coordinate along the axis along which the regions of the examination object, imaged by the first and the second image, are adjacent to one another.

The first image and the second image can be transformed by each being registered elastically against the superposed image. Here, elastic registration of an image against another image is understood to be a transformation of the image which amplifies a similarity in the region common to the image and the other image and which can lead to a change of distances between image features within the transformed image.

The determination and transformation steps can be repeated iteratively. In the process, during iteration, a further superposed image is determined using the weighting function as a weighted superposition of the transformed first and second images determined in the preceding iteration. The quality of the superposed image as a reference image can be improved iteratively by always determining new superposed images.

The first image or the second image can be transformed such that a grid of data points is defined and a deformation vector associated with each data point is determined. The deformation vectors can be determined by maximizing a similarity measure between the superposed image and the first image or the second image. In the process, forced conditions can be imposed to suppress strong variations of the deformation vector field on small spatial scales. This makes it possible to transform the first image and the second image using a free form deformation (FFD).

The overall image, which illustrates the desired combination of the first image and the second image, can be generated as a weighted superposition of the transformed first image and second image determined in the final iteration. The overall image is advantageously generated from the transformed first and second images using the same weighting function which was used in the preceding iterations for determining the superposed image.

The method can be used to combine MR records or images generated on the basis of MR records. The method is not restricted to combining two MR records, but can be used in a corresponding fashion to combine a relatively large number of MR records. For example, this makes it possible to generate an MR whole-body image, the resolution of which substantially corresponds to the resolution of the individual MR records.

Even though the method determines an initial reference image for the transformation of the first and the second image on the basis of the first and the second image, the method can utilize additional information to further compensate for distortions in the first and second images.

For example, it is possible to record a control image using a "move during scan" method and register the superposed image against said control image before the first image and the second image are subject to elastic registration against the superposed image. In the "move during scan" method, MR imaging is effected during substantially continuous movement of the object couch. Since the imaging is effected in the vicinity of the magnetic isocenter, the control image typically has a relatively weak distortion, particularly compared to MR records with a large FOV. If the superposed image is first of all registered against the control image with only weak distortion, the distortions in the reference image generated in this way are reduced.

Alternatively, or additionally, it is also possible to take account of information relating to system-dependent, i.e. due to the coil geometry in particular, inhomogeneities of the B0 field or spatial variations of magnetic field gradients. As long as the distortions caused by system-dependent inhomogeneities of the B0 field or by spatial variations of magnetic field gradients are known, MR records can first of all be subject to a predetermined transformation which reduces or removes the system-dependent distortions. Applying the predetermined transformation to MR records thus makes it possible to generate the first and the second image to which the method for combining images is subsequently applied. The predetermined transformation can be determined by positions of known object points of a sample body being determined by measurement of at least one sample body and being compared to positions of corresponding image features in order to determine a distortion vector field. The predetermined transformation can then be defined as the inverse function of the distortion determined on the sample body.

A magnetic resonance scanner according to at least one embodiment of the invention comprises a recording device for recording a first MR record and a second MR record of an examination object, wherein the first MR record and the second MR record have an overlap region, and a processor designed to combine the first MR record and the second MR record by using the method according to the invention.

According to at least one embodiment of the invention, a computer program product with a succession of commands stored therein is also specified, which computer program product effects the execution of the method according to an example embodiment on an electronic processing unit when executed by a processor of the electronic processing unit.

At least one embodiment of the method according to the invention can advantageously be used to combine MR records. For example, by using the method according to the invention it is possible to combine a number of MR records to form an MR whole-body image. However, the method according to at least one embodiment of the invention is not restricted to this field of application.

BRIEF DESCRIPTION OF THE DRAWINGS

In the following text, example embodiments of the invention will be explained in more detail with reference to the attached drawing.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
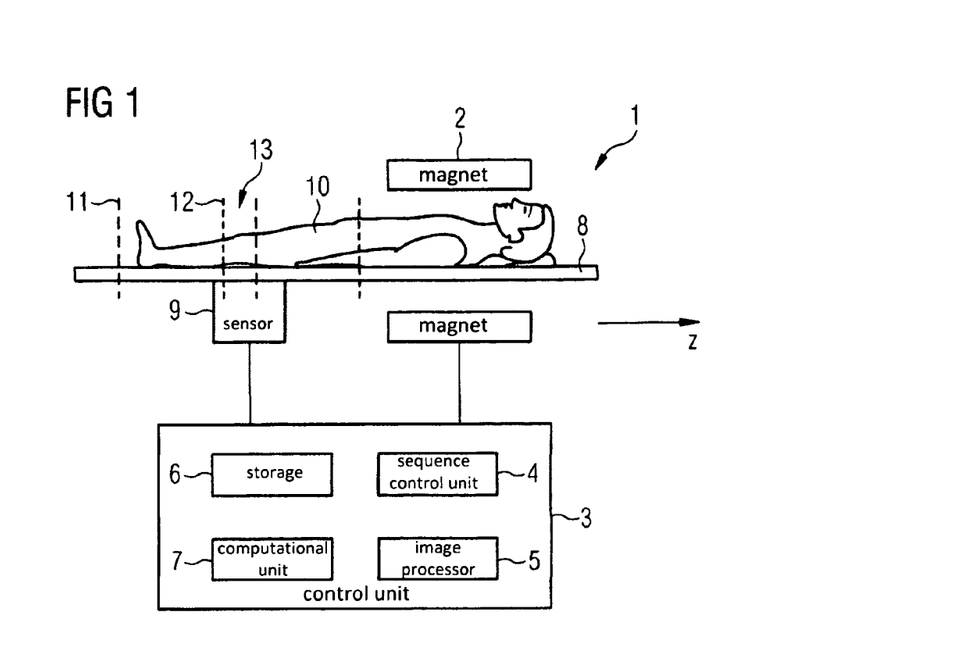
FIG. 1 is a schematic illustration of a magnetic resonance scanner according to an embodiment of the invention.

FIG. 1 shows an MR scanner 1 which can be used to generate MR records and combine the latter to form an overall image. The MR scanner has a magnet 2 for generating a polarization field $B_0$, which can, for example, be aligned along the z direction. In order to generate MR records, provision is furthermore made for a gradient system for generating magnetic field gradients, a radiofrequency (RF) system for radiating RF pulses into the scanner, and coils for detecting the signals induced by the RF radiation; these are not illustrated in FIG. 1. A control unit 3 of the MR scanner 1, used to control the MR imaging procedure, comprises a pulse sequence control unit 4, an image processor 5 which generates an MR record on the basis of the detected signals, and a storage 6 for saving the MR records. The general mode of operation of an MR scanner 1, which generates MR records by irradiation with RF pulses and switching gradients to locate the detected signals, is known to a person skilled in the art and will not be explained in any more detail. For reasons of clarity, only those elements which are important for understanding the present invention will be explained in more detail in the following text.

The control unit 3 also has a computational unit 7, for example a processor which has been designed in a suitable fashion by programming, which combines a number of MR records to form an overall image. In order to generate the number of MR records, a patient 10 lying on an examination couch 8 is displaced relative to the magnet 2 and an MR record of a region of the patient 10 arranged in the magnet 2 is generated. A sensor 9 coupled to the examination couch 8, which sensor can for example be integrated in the motor drive of the examination couch 8, registers a position of the examination couch 8 in the z direction and outputs said position to the computational unit 7.

The displacement of the examination couch 8 makes it possible to generate sequential MR records of a number of regions 11, 12 of the patient, the boundary regions of which MR records are illustrated schematically using pairs of dashed lines. The regions 11, 12 and the corresponding MR records have an overlap region 13. Inhomogeneities of the B0 field and nonlinearities of gradient fields lead to the MR records of the regions 11, 12 being distorted in the overlap region 13. This typically leads to the MR records of the regions 11, 12 not corresponding to one another in the overlap region 13.

Figure 2:
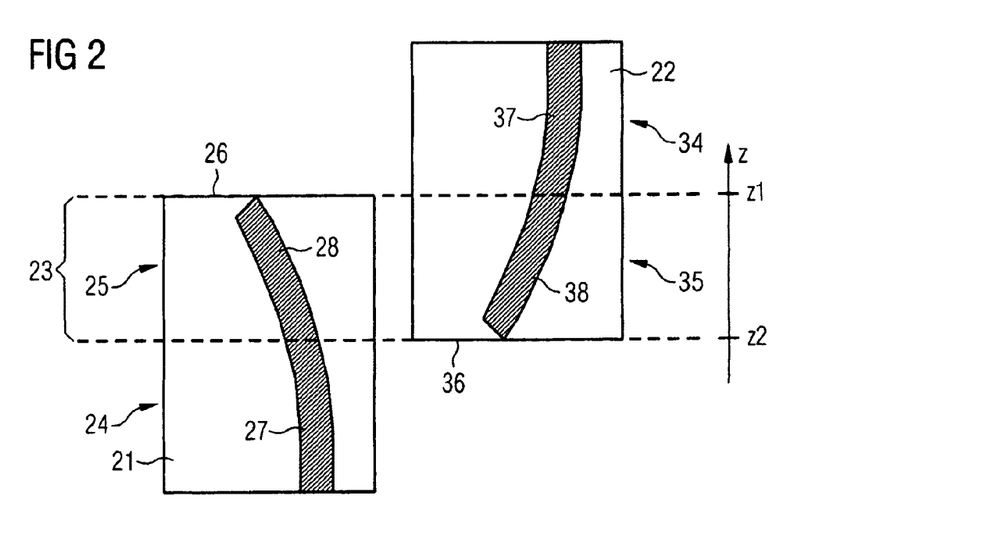
FIG. 2 shows example first and second images in order to explain the method according to the invention.

FIG. 2 shows an example first image 21 and an example second image 22 which have an overlap region 23. These images, which represent regions of an object which are adjacent to one another along the z-axis, illustrate for example MR records of the regions of the patient 10 in FIG. 1 referred to by 11 and 12. The example first image 21 has an image region 24 which does not overlap with the second image 22, and an image region 25, which does overlap with the second image 22. The first image 21 shows a structure 27 of an imaged object. The second image 22 has an image region 34, which does not overlap with the first image 21, and an image region 35, which does overlap with the first image 21. The example second image 22 shows a structure 37 of the imaged object.

The boundaries of the overlap region 23, in which both image data of the first image 21 and image data of the second image 22 are present, are defined by an image edge 26 of the first image 21 at the z-coordinate z1 and by an image edge 36 of the second image 22 at a z-coordinate z2. Due to imaging errors, a section 28 of the structure 27 in the first image 21 located in the overlap region 23 and a section 38 of the structure 37 in the second image 22 located in the overlap region are not congruent.

One option for combining MR records to form an overall image with reduced discontinuities, despite the deviations in the overlap region, includes transforming the MR records using the coordinate transformations $T_1(\bullet)$ and $T_2(\bullet)$ such that $$E = \int_{V\cap} \rho(I_1(T_1(\vec{x})), I_2(T_2(\vec{x}))) d^D \vec{x} \qquad (1)$$

is minimized. Here, $\rho(\bullet)$ refers to a local distance or difference measure, $I_1(\bullet)$ to the intensity or brightness of the first image, $I_2(\bullet)$ to the intensity or brightness of the second image and D=2 or 3 to the dimension of the images. The vector $\vec{x}=(x,z)$ or $\vec{x}=(x,y,z)$ refers to the coordinates of the pixels in D=2 or D=3. $T_1(\bullet)$ and $T_2(\bullet)$ are functions which should be determined such that the functional E in equation (1) is minimized.

In conventional methods for combining images, the value E specified in equation (1) is for example minimized by defining $T_2(\bullet)$ as the identity map and determining the transformation $T_1(\bullet)$. In this case, the second image $I_2(\bullet)$ serves as a reference image against which the first image $I_1(\bullet)$ is registered.

The computational unit 7 of the MR scanner 1 according to an embodiment of the invention is designed to execute a method described in more detail below with reference to FIGS. 3-14. In this method, a reference image is first of all generated from the two images to be combined, against which reference image both the first and the second image are registered.

Figure 3:
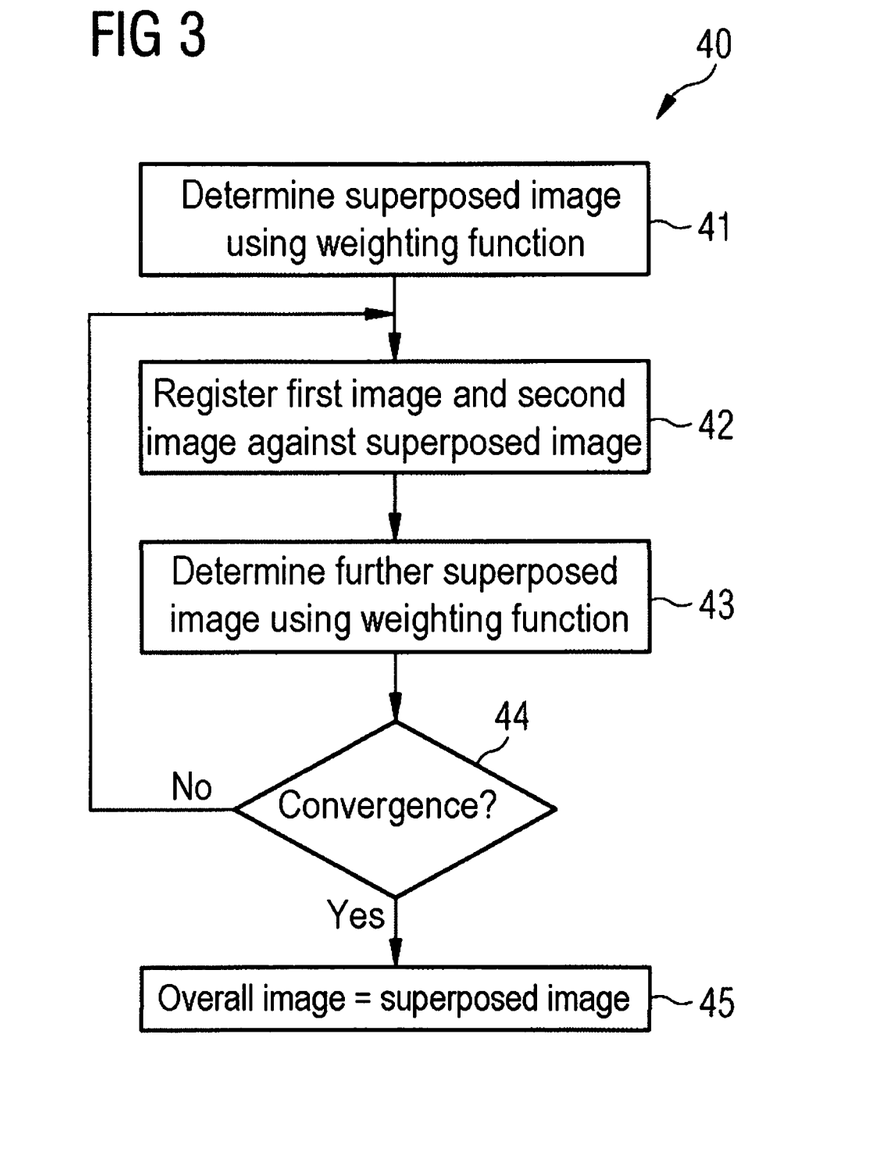
FIG. 3 shows a flowchart of a method according to an embodiment of the invention.

FIG. 3 shows a flowchart of a method 40 according to an embodiment of the invention, by which a number of images can be combined to form an overall image.

In step 41, a superposed image is firstly determined on the basis of the first image and the second image. As explained in more detail below, the superposed image in the overlap region is defined as a weighted superposition of the first image and the second image, the weighting function in the overlap region being variable in space. In step 42, the first image is transformed on the basis of a comparison of the first image with the superposed image determined in step 41, and the second image is transformed on the basis of a comparison of the second image with the superposed image determined in step 41. The first and the second image are transformed by an elastic registration of the respective image against the superposed image, a difference measure between the respective image and the superposed image serving as a reference image being reduced in the process. In step 43, a further superposed image is determined as a superposition weighted with the weighting function of the transformed first image and the transformed second image. Subsequently, steps 42 and 43 can be repeated iteratively. A convergence criterion is checked in step 44. As soon as there is sufficient convergence in the superposed image, the last determined superposed image is fixed in step 45 as the overall image which was combined from the first image and the second image.

The method 40 determines a superposed image from the images to be combined, with the superposed image serving as a reference image for the subsequent transformation of the first and second image. As will be explained in more detail below, a suitable definition of the weighting function used in steps 41 and 43 can take into account that the strength of distortions often varies spatially within images. In particular, the weighting function can be selected such that sections of the first and the second image in which strong distortions are expected only contribute a relatively small amount to the superposed images determined in steps 41 and 43.

The superposed image $S(\bullet)$ determined in step 41 can be defined region-by-region as follows for the overlap region V0 of the first and second image; the region of the first image V1\V0 not located in the overlap region V0; and the region of the second image V2\V0 not located in the overlap region V0:

$$S(\vec{x})=f(\vec{x}) \text{ if } \vec{x} \in V0, \tag{2a}$$

$$S(\vec{x})=I_1(\vec{x}) \text{ if } \vec{x} \in V1\backslash V0 \text{ and} \tag{2b}$$

$$S(\vec{x})=I_2(\vec{x}) \text{ if } \vec{x} \in V2\backslash V0. \tag{2c}$$

Here, the function $f(\bullet)$ is defined in the overlap region V0 as the weighted linear superposition of the first image $I_1(\bullet)$ and the second image $I_2(\bullet)$:

$$f(\vec{x})=(1-h(\vec{x})) \cdot I_1(\vec{x})+h(\vec{x}) \cdot I_2(\vec{x}). \tag{3}$$

Hence, when the superposed image is determined for the first time in step 41, the superposed image is generated as a weighted superposition of the first and second images which have not yet been transformed.

The weighting function $h(\bullet)$, having a value between 0 and 1, determines the weighting of the first and the second image in the overlap region of the superposed image $S(\bullet)$ as a function of location.

The weighting function $h(\bullet)$ can vary spatially in the overlap region V0. The weighting function $h(\bullet)$ is preferably selected such that in regions in which significant distortions of the second image $I_2(\bullet)$ are expected, it has a small value and in regions in which significant distortions of the first image $I_1(\bullet)$ are expected, it has a value close to 1.

The weighting function $h(\bullet)$ does not have to vary as a function of each of the D spatial coordinates. $h(\bullet)$ is preferably a monotone function. For example, the weighting function $h(\bullet)$ can be defined as a linear function of a coordinate z along the axis along which the first and second images are adjacent:

$$h(\vec{x}) = \frac{z-z2}{z1-z2}. \tag{4}$$

This selection of the weighting function $h(\bullet)$ takes into account the typically larger distortions of MR records in the vicinity of the edges in the read-out direction.

The superposed image $S(\bullet)$ determined in the subsequent iterations in step 43 can in turn be defined, region-by-region, as follows:

$$S(\vec{x})=f(\vec{x}) \text{ if } \vec{x} \in V0, \tag{5a}$$

$$S(\vec{x})=I_1(T_1(\vec{x})) \text{ if } \vec{x} \in V1\backslash V0 \text{ and} \tag{5b}$$

$$S(\vec{x})=I_2(T_2(\vec{x})) \text{ if } \vec{x} \in V2\backslash V0. \tag{5c}$$

Here, the function $f(\bullet)$ is defined in the overlap region V0 as the weighted linear superposition of the first transformed image $I_1(T_1(\bullet))$ and the second transformed image $I_2(T_2(\bullet))$:

$$f(\vec{x})=(1-h(\vec{x})) \cdot I_1(T_1(\vec{x}))+h(\vec{x}) \cdot I_2(T_2(\vec{x})). \tag{6}$$

Here, $T_1(\bullet)$ and $T_2(\bullet)$ refer to the transformations of the first and the second image last determined in step 42. The weighting function $h(\bullet)$ is defined as in step 41, that is to say it can vary as a function of z, as specified in equation (4).

The method 40 will still be explained in more detail in an example fashion with reference to FIGS. 4 to 7.

Figure 4:
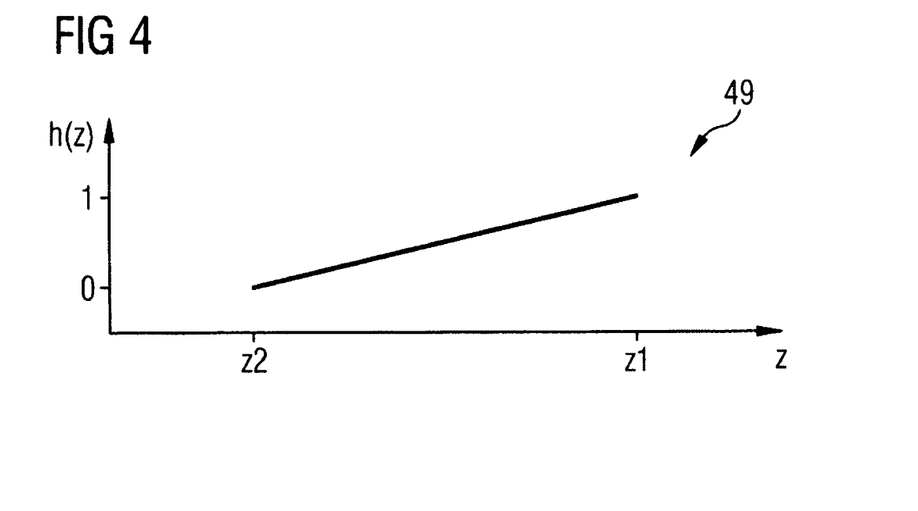
FIG. 4 shows a weighting function that can be used in the method as per FIG. 3.

FIG. 4 graphically illustrates 49 the weighting function h(z) defined in equation (4). In the overlap region bounded by the z-coordinates of the image edges of the first image and the second image, the example weighting function $h(\bullet)$ is a linear function of the z-coordinate.

Figure 5:
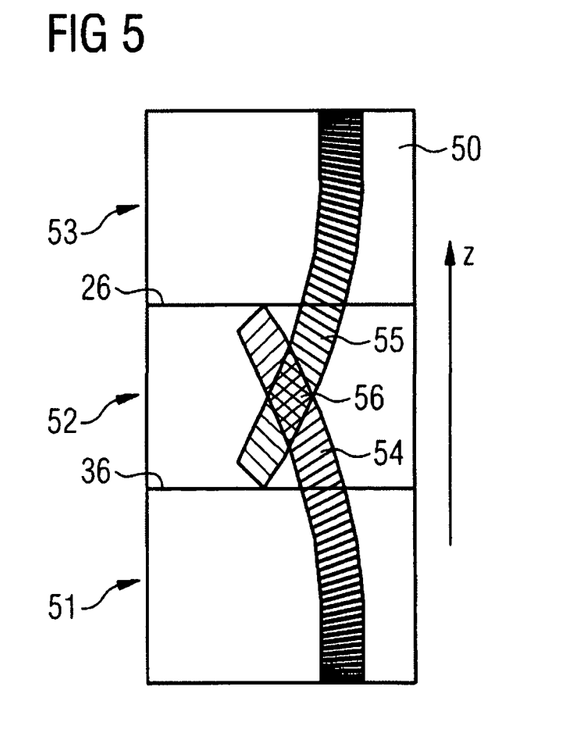
FIG. 5 shows a superposed image generated from the images illustrated in FIG. 2.

FIG. 5 is a schematic illustration of a superposed image 50 which is determined by the first and the second images 21, 22 illustrated in FIG. 2. The superposed image 50 is determined in step 41 in the method 40 in FIG. 3.

The superposed image 50 has three image regions 51, 52 and 53. Image region 51 corresponds to the region of the first image which does not overlap with the second image. In image region 51, the superposed image is defined by equation (2b). Image region 53 corresponds to the region of the second image which does not overlap with the first image. In image region 53, the superposed image is defined by equation (2c). Thus, image regions 51 and 53 of the superposed image 50 are identical to the corresponding regions of the first and the second image, respectively. Image region 52 corresponds to the overlap region of the first image and the second image, in which the superposed image is defined by equation (2a). Due to the spatially varying weighting function, the weighting of pixels of the first image is continually reduced in image region 52 in the direction of the edge of the overlap region 52 which corresponds to the edge 26 of the first image. Similarly, the weighting of pixels of the second image is continually reduced in the overlap region 52 in the direction of the edge 36 which corresponds to the edge 36 of the second image, as can be seen, for example, in the intensity variations of the structures 54 and 55 which originate from the first image and the second image, respectively. The superposed image 50 still has discontinuities, for example at the intersection 56, which are caused by the distortions of the first image and the second image.

The transformation of the first and the second image in step 42 of the method 40 as per FIG. 3 is effected by elastic registration of the first image and the second image against the superposed image. For example, to this end, the coordinate transformations $T_1(\bullet)$ for the first image $I_1(\bullet)$ and $T_2(\bullet)$ for the second image $I_2(\bullet)$ can be determined such that $$E = \sum_{j=1,2} \int_{V0} \rho(S(\vec{x}), I_j(T_j(\vec{x}))) d^D \vec{x}. \quad (7)$$

is minimized. Here, $\rho(\bullet)$ again refers to a local distance or difference measure. Various suitable distance measures are known from image processing. For example, the squared difference of pixel values, $$\rho(S(\vec{x}), I_j(T_j))) \propto (S(\vec{x}) - I_j(T_j(\vec{x})))^2, \quad (8)$$

can be used as a distance measure. Alternative distance measures comprise, for example, the so-called interaction information or Shannon-Wiener entropy.

Since the variable E of equation (7) can be minimized by mutually independent transformations $T_1(\bullet)$ for the first image and $T_2(\bullet)$ for the second image, only transformation $T_1(\bullet)$ is described in more detail below with reference to FIGS. 6-10. The explanations also apply to the transformation $T_2(\bullet)$.

Figure 6:
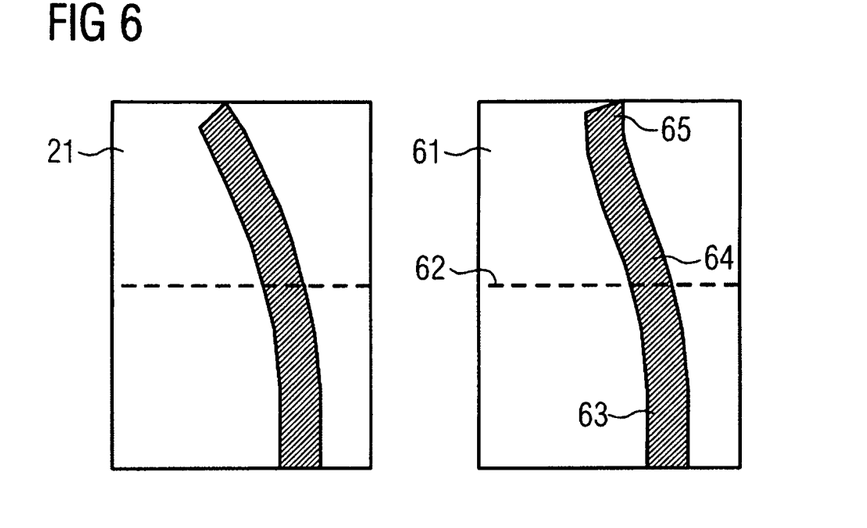
FIG. 6 shows the original first image from FIG. 2 (left half of the figure) compared to a transformed first image (right half of the figure) generated using the method from FIG. 3.

FIG. 6 shows a transformed first image 61 compared to the original first image 21. The transformed first image 61 is generated by elastic registration of the first image 21 against the superposed image 50. A dashed line schematically shows a boundary 62 of the overlap region which corresponds to the edge of the second image. The structure 63 is only changed slightly outside of the overlap region. Compared to the original first image 21, the transformed first image 61 is deformed more strongly within the overlap region. Here, the magnitude of the deformation increases from the boundary 62 of the overlap region, for example at a section 64, to the edge of the transformed first image 61. A position of a section 65 of the structure 63 which is arranged in the vicinity of the edge of the transformed first image 61 moves more strongly in the direction of the position of the corresponding structure in the second image. It is expected that in this spatial area, i.e. in the vicinity of the edge of the first image, the second image has less distortion than the first image. As a result of the elastic registration of the first image against the superposed image sketched in FIG. 6, there is thus convergence toward image data which are expected to typically have less distortion.

Even if this is not illustrated in FIG. 6, the second image is also transformed in a corresponding manner by elastic registration against the superposed image.

Figure 7:
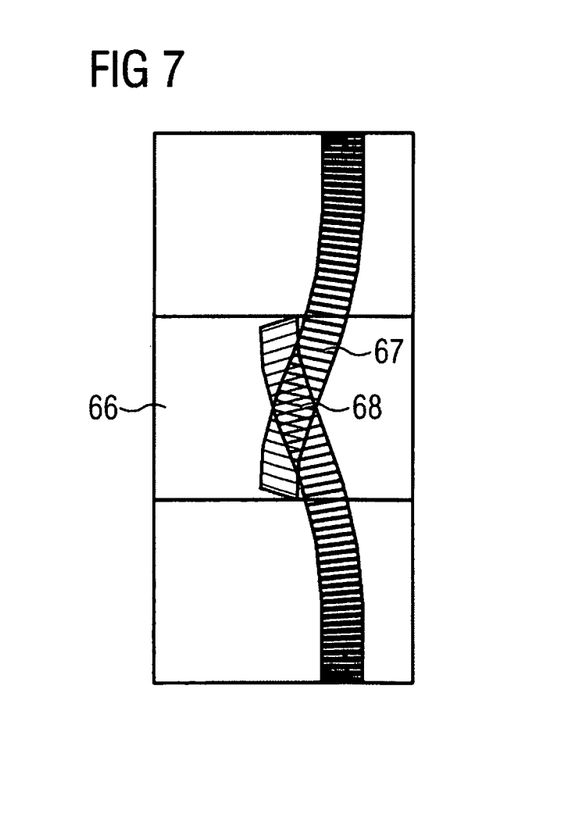
FIG. 7 shows a further superposed image generated using the method from FIG. 3.

FIG. 7 shows an example further superposed image 66. The further superposed image 66 is generated by the weighted superposition of the transformed first image 61 and the correspondingly transformed second image. In the method 40 as per FIG. 3, the further superposed image is generated in step 43.

The further superposed image 66 shows a structure 67 which is smoothed compared to the corresponding structure in the originally generated image 50. For example, a kink in an edge line of the structure 67 at the intersection 68 is less pronounced than the corresponding kink at the intersection 56 of the superposed image 50 in FIG. 5. This smoothing is further improved with an increasing number of iterations.

In order to be able to realize the elastic registration sketched out in FIG. 6, different methods can be utilized to minimize the functional specified in equation (5). In the following text, registration using the so-called free-form deformation is described in an example fashion, in which in each case a grid $G_1$ or $G_2$ of data points p is superposed on the first or second image to be transformed. Points in a prescribed neighborhood of a data point p are displaced according to the equation $$T_j(\vec{x}) = \vec{x} + \vec{d}(\vec{p}) \quad (9)$$

by a displacement vector d which is determined as a function of the respective data point p such that the contribution of the neighborhood of the data point p to the functional E in equation (5) is reduced. That is to say, the displacement vector associated with the data point p is selected such that the neighborhood of the data point p is brought into an agreement which is as good as possible with a region of the reference image, i.e. the superposed image $S(\bullet)$.

Figure 9:
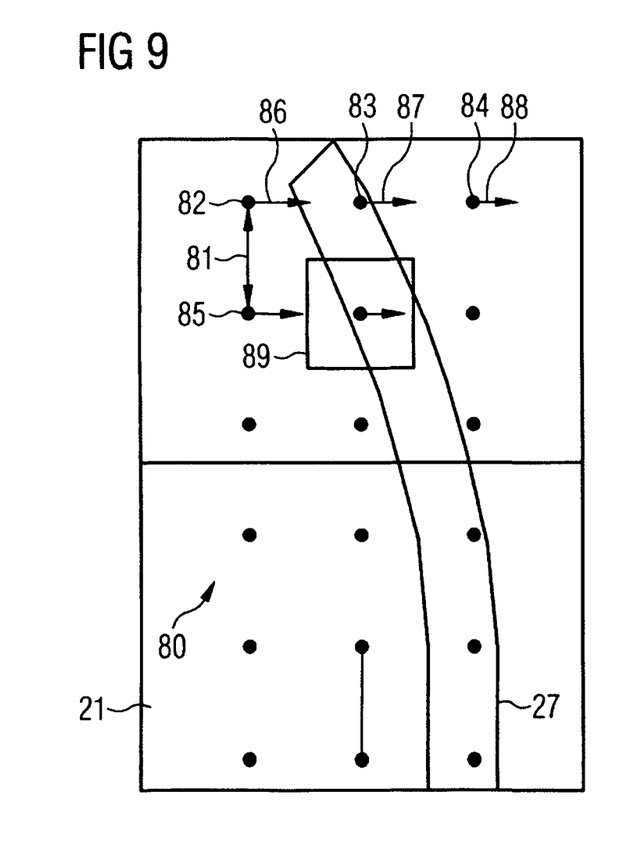
FIG. 9 and FIG. 10 are schematic illustrations which show the use of different data point grids.

For a further explanation of these method steps, reference is made to FIG. 9. FIG. 9 shows the first image 21 from FIG. 2, with the structure 27 only being illustrated in outline for reasons of clarity. A grid 80 of data points is superposed on the first image 21. A plurality of data points in a regular arrangement with a prescribed spacing 81 between adjacent data points are illustrated schematically. A deformation vector 86 to 88 is determined for the data points, for example for each data point 82 to 85. By way of example, the deformation vector can be selected from a finite number of possible deformation vectors. For each data point, the corresponding deformation vector is selected such that correspondence of the first transformed image with the reference image, i.e. with the superposed image, is increased. FIG. 9 also sketches a neighborhood 89 of a data point. Once the deformation vectors are determined for each of the data points, the neighborhood of each data point is displaced, as per the deformation vector associated with the data point, as specified in equation (9).

The registration of the first and the second image against the superposed image $S(\bullet)$ can be determined not only by using a single grid, but also iteratively using a number of grids of data points with decreasing data point spacing a. If t refers to the current iteration step, a deformation vector is in turn determined for each data point p in this iteration step. Points in a neighborhood of the data point p are displaced according to the equation $$T_j^{(t)}(\vec{x}) = T_j^{(t-1)}(\vec{x}) + \vec{d}^{(t)}(\vec{p}), \quad (10)$$

where the first term on the right-hand side of equation (8) describes the displacement determined in the preceding iterations and the second term describes the deformation vector for the neighborhood of the data point p, which was newly determined in the iteration t.

Figure 8:
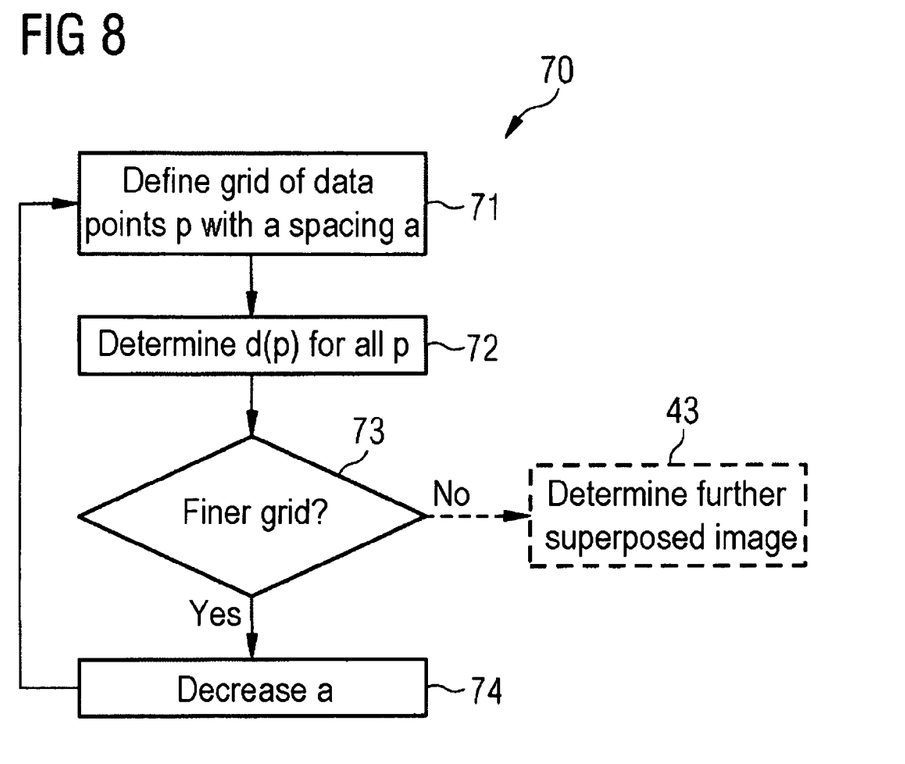
FIG. 8 shows a flowchart of method steps for transforming images.

FIG. 8 shows a flowchart of a sequence of method steps which can be used to transform the first and the second image in step 42 of the method 40 in FIG. 3. The method steps 70 use a hierarchy of more and more refined grids of data points.

A grid of data points with a predetermined spacing a is defined in step 71. Step 72 determines the deformation vector associated with a data point for every data point. If it is subsequently determined in step 73 that a further refinement of the data point grid is desirable, a new grid of data points with smaller grid spacing is defined in steps 74 and 71. Each refinement of the data point grid makes it possible, for example, to define other deformation vectors, specifically shorter permitted ones. Steps 74 and 71 are iterated until the decision step 73 determines that no further refinement of the grid is possible or necessary. The transformation of the first and the second image determined when the iteration is aborted corresponds to the transformation in step 42 of method 40 in FIG. 2. The correspondingly transformed first image and transformed second image are used to determine the further superposed image in step 43.

Figure 10:
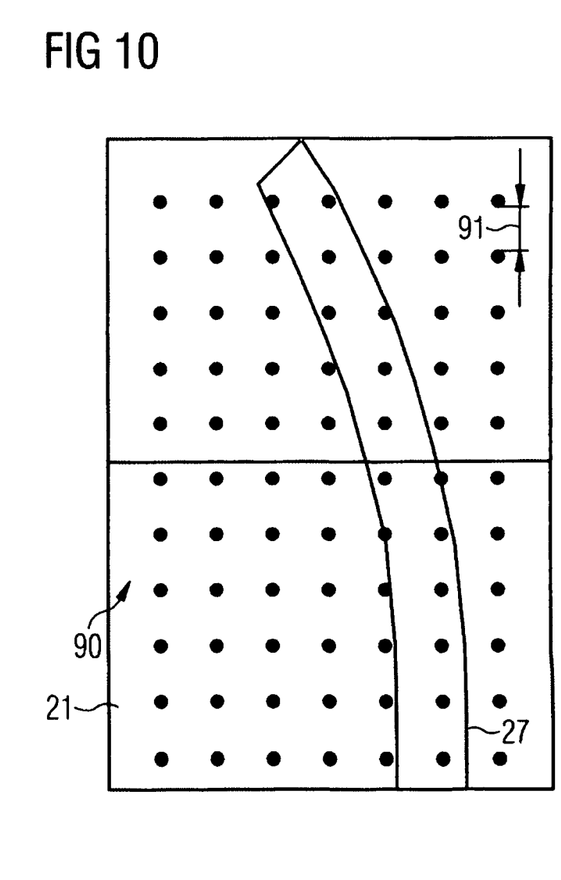

A plurality of different data point grids with different data point spacings are sketched in FIGS. 9 and 10. FIG. 9 shows a first grid 80 with a first data point spacing 81, while FIG. 10 shows a second grid 90 of data points with a second data point spacing 91.

Although free form deformation affords the possibility of respectively defining the data point grid or grids only in the overlap region of the first and the second image, the data point grid advantageously also covers those regions of the first and the second image which do not lie in the overlap region. By also deforming those regions adjacent to the overlap region, a continuous deformation vector field can be ensured. In the case of free form deformation, a term in the functional E of equation (7) can to this end additionally be taken into account; this term increases the value of the functional E in the case of strong spatial fluctuations of the deformation vector field and thus enforces a forced condition to suppress strong spatial fluctuations of the deformation vector field.

While the method described above with reference to FIGS. 2 to 10 generates an overall image exclusively on the basis of the first image and the second image, the method according to an embodiment of the invention can also use further information for generating the overall image.

Figure 11:
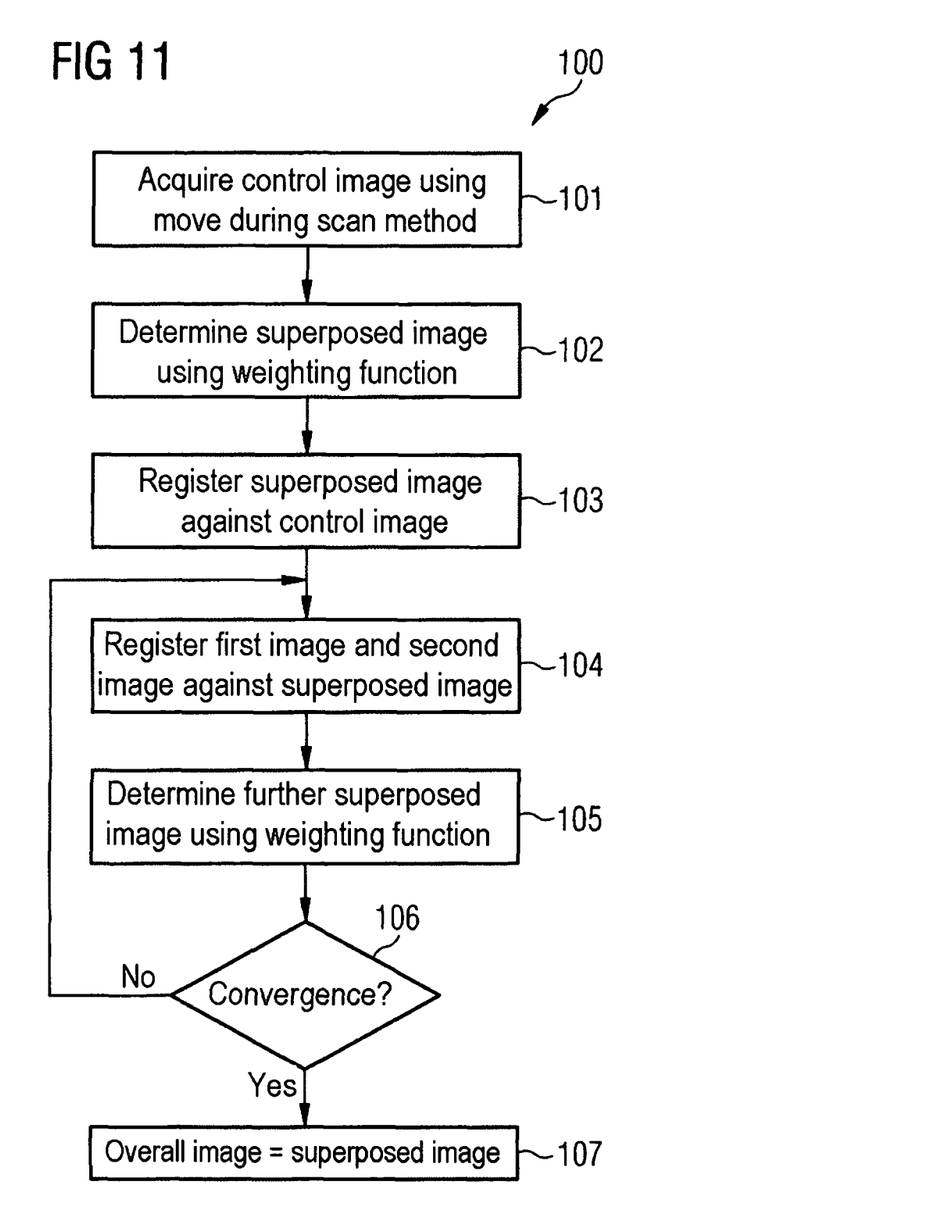
FIG. 11 shows a flowchart of a method according to a further example embodiment.

FIG. 11 shows a flowchart of a method 100 for combining a number of images according to a further example embodiment. In the method 100, a control image is additionally created with the aid of a so-called "move during scan" method and used when combining the images.

In step 101, the control image is generated using the movement during scan method. In this method, MR imaging is effected during substantially continuous movement of the object couch. A superposed image is determined in step 102 as a weighted superposition of a first image and a second image. Step 102 is effected as explained with reference to step 41 in FIG. 3. In step 103, the superposed image is registered against the control image. Since the control image generated by the move during scan method typically has a lower resolution, but also less distortion and, in the ideal case, is substantially free from distortions, registering the superposed image against the control image in step 103 can generate an improved reference image for the subsequent elastic registration of the first and the second image.

Steps 104 to 107 of the method 100, in which the first image and the second image are transformed, a further superposed image is generated, a check is performed as to whether the convergence criteria are satisfied and dependent thereon a new iteration is carried out or the current superposed image is determined as the generated overall image, correspond to steps 42 to 45 of method 40 in FIG. 3 and so a more detailed explanation can be dispensed with.

In a modification of the method 100 according to a further example embodiment, not only the superposed image determined in step 102 but also the superposed image respectively generated in every iteration is elastically registered against the control image.

Figure 12:
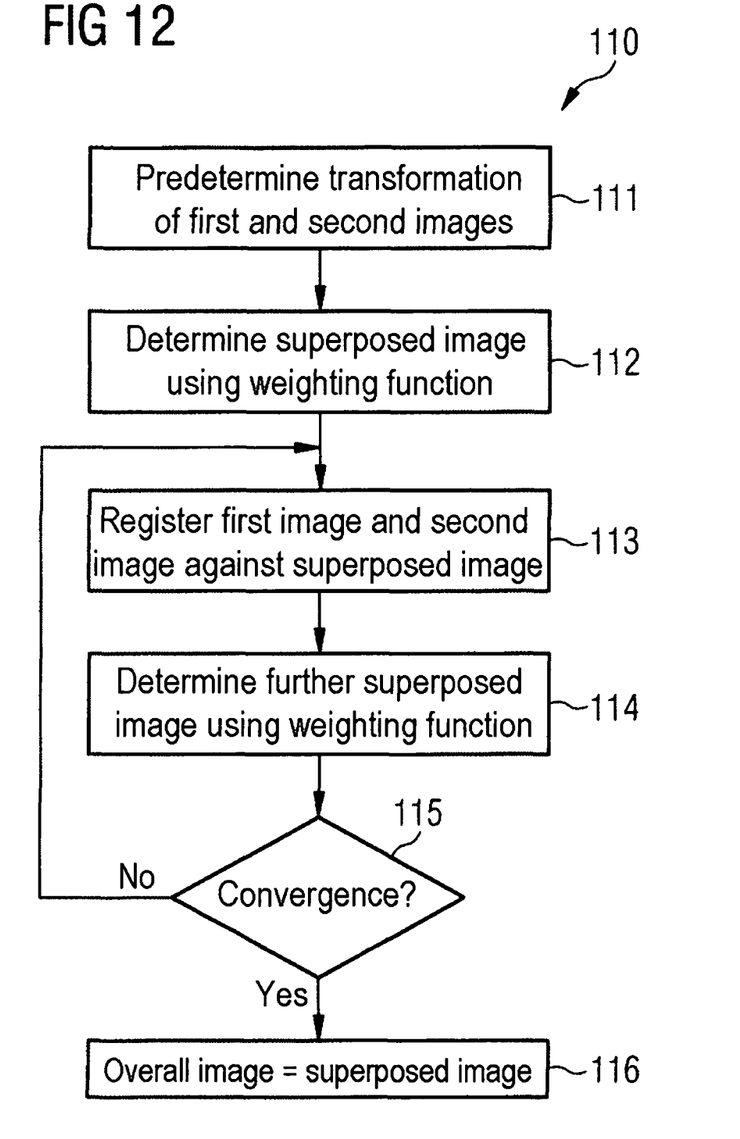
FIG. 12 shows a flowchart of a method according to an additional further example embodiment.

FIG. 12 shows a flowchart of a method as per a further example embodiment. The method takes account of additional information regarding system-dependent, i.e. due to the coil geometry in particular, inhomogeneities of the B0 field or spatial variations of magnetic field gradients. Such system-dependent variations of magnetic fields and magnetic field gradients lead to a system-dependent distortion. In the method 110, the system-dependent distortion is taken into account by a predetermined transformation of the first and the second image to reduce the influence of system-dependent distortions or, in an ideal case, remove them.

To this end, a predetermined transformation is applied to the first and the second image in step 111. The predetermined transformation is defined such that it substantially compensates system-dependent distortions. In order to determine the parameters of the predetermined transformation, for example in the form of a deformation vector field associated with this transformation, a sample body with known geometry can be subject to the MR imaging. By comparing the MR record of the sample body with the known geometry thereof, it is possible to determine the distortion vector field. The predetermined transformation is defined as the transformation which maps the MR record of the sample body back onto the actual geometry thereof. Since the resultant distortions when measuring a sample body are not only system-dependent, but also object-dependent, these steps are advantageously effected with a number of sample bodies. The predetermined transformation can then be determined on the basis of the MR records of the different sample bodies and the actual geometries thereof.

After the first and the second image were subject to the predetermined transformation, the method 110 effects method steps 112 to 116, which correspond to method steps 41 to 45 in FIG. 3, starting with the first and second images transformed in this way. Thus, a detailed explanation of these method steps can be dispensed with.

The application of a predetermined transformation on the first and the second image to compensate for system-dependent distortions as described with reference to FIG. 12 can also be combined with the use of a control image, as described with reference to FIG. 11.

Figure 13:
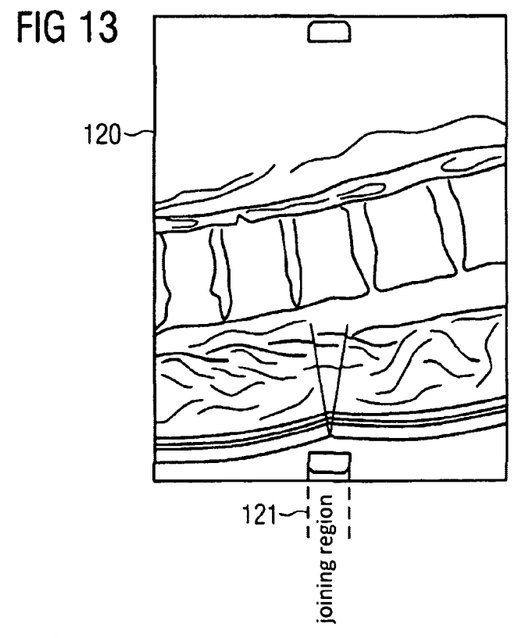
FIG. 13 shows an initial superposition of MR records and FIG. 14 shows an overall image generated by the method according to an embodiment of the invention.
Figure 14:
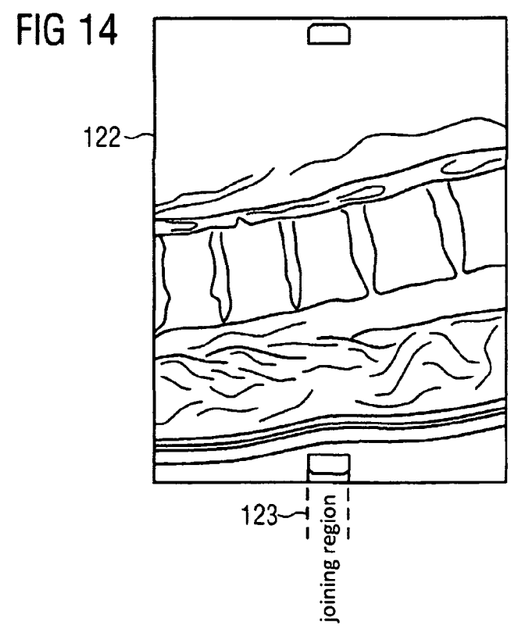

FIGS. 13 and 14 illustrate the application of the method according to the invention to MR records. FIG. 13 and FIG. 14 respectively show a section of a superposed image generated from two MR records of a spinal column. The superposed images were each generated as a weighted superposition of two adjacent images using the weighting function specified in equation (4). FIG. 13 shows a superposed image 120 which was generated as a weighted superposition of the originally recorded first and second images. The superposed image 120 has signatures of distortions of the individual records in an overlap region 121 of the adjacent MR records signified by a bright bar.

FIG. 14 shows a superposed image 122 which was generated by a number of iterations of an elastic registration against the superposed image and by determining a new superposed image from the images transformed in this fashion. Artifacts due to distortions of the individual images in the edge regions thereof are reduced in the joining region 123 of the superposed image 122 compared to the joining region 121 of the superposed image 120.

Although the invention was described with reference to advantageous or example embodiments, the invention is not restricted to these example embodiments. Thus, for example, the weighting function does not have to be a linear function. For example, the weighting function can be a nonlinear function of the coordinate along the axis along which the two images to be combined are adjacent. In particular, the weighting function can be selected as a nonlinear function which takes account of the spatial variation of image distortions in the vicinity of the image edge.

Although the method according to at least one embodiment the invention can advantageously be used when combining a number of MR records, it is not restricted to this specific application. For example, the method according to at least one embodiment of the invention can similarly be used to combine two-dimensional and three-dimensional images.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks.

Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for combining a first image and a second image of an examination object, the first and second images including an overlap region, the method comprising:
   determining a superposed image as a weighted superposition of the first image and the second image in the overlap region, with a weighting function which represents a weight of at least one of the first image and the second image at positions in the superposed image being spatially variable in the overlap region;
   transforming the first image and the second image on the basis of a comparison of at least one of the first image and the second image with the determined superposed image;
   determining a further superposed image from the transformed first image and the transformed second image; and
   generating an overall image from the further superposed image when at least one convergence criterion is satisfied, wherein
      the superposed image of the first and the second image is used as a reference image for the transformation of the first and the second image.

2. The method as claimed in claim 1, wherein the first image and the second image show regions of the examination object which are adjacent to each other along an axis, wherein the weighting function is variable in the overlap region along the axis.

3. The method as claimed in claim 2, wherein the weighting function in the overlap region is a mainly monotonic function of a coordinate along the axis.

4. The method as claimed in claim 2, wherein the weighting function is selected such that a weighting of pixels of the first image relatively decreases in the overlap region in the direction of an edge of the first image, and wherein a weighting of pixels of the second image relatively decreases in the overlap region in the direction of an edge of the second image.

5. The method as claimed in claim 1, wherein the weighting function is selected such that a weighting of pixels of the first image relatively decreases in the overlap region in the direction of an edge of the first image, and wherein a weighting of pixels of the second image relatively decreases in the overlap region in the direction of an edge of the second image.

6. The method as claimed in claim 1, wherein the first and the second image are each respectively registered elastically against the superposed image in order to transform the first image and the second image.

7. The method as claimed in claim 1, wherein the determining a superposed image and the transforming are repeated iteratively.

8. The method as claimed in claim 7, wherein, during the iteration, a further superposed image is determined using the weighting function as a weighted superposition of the transformed first image and the transformed second image.

9. The method as claimed in claim 1, wherein a multiplicity of deformation vectors associated with data points are determined to transform at least one of the first image and the second image.

10. The method as claimed in claim 9, wherein at least one of the first image and the second image is transformed under forced conditions which suppress large changes of deformation vectors associated with adjacent data points.

11. The method as claimed in claim 10, wherein a number of grids of data points are used iteratively to transform at least one of the first image and the second image, a spacing between the data points being reduced iteratively.

12. The method as claimed in claim 9, wherein a number of grids of data points are used iteratively to transform at least one of the first image and the second image, a spacing between the data points being reduced iteratively.

13. The method as claimed in claim 1, wherein the overall image is generated as a weighted superposition of the transformed first image and the transformed second image.

14. The method as claimed in claim 1, wherein the first image and the second image are each generated on the basis of a magnetic resonance record.

15. The method as claimed in claim 14, wherein a control image is recorded using a move during scan method and the superposed image is transformed on the basis of a comparison of the superposed image with the control image before the first image and the second image are transformed.

16. The method as claimed in claim 15, wherein the first image is generated from a transformation of a first magnetic resonance record and the second image is generated from the transformation of a second magnetic resonance record.

17. The method as claimed in claim 14, wherein the first image is generated from a transformation of a first magnetic resonance record and the second image is generated from the transformation of a second magnetic resonance record.

18. The method as claimed in claim 17, wherein the transformation takes account of at least one of system-dependent magnetic field distortions and changes in gradient fields.

19. The method as claimed in claim 18, wherein the transformation is deduced from a measurement of at least one sample body.

20. The method as claimed in claim 17, wherein the transformation is deduced from a measurement of at least one sample body.

21. The method as claimed in claim 14, wherein the method is used for generating a whole-body image.

22. A computer program product stored on a non-transitory computer readable medium with a succession of commands stored therein, causing the execution of the method as claimed in claim 1 on an electronic processing unit when executed by a processor of the electronic processing unit.

23. A non-transitory computer readable medium including program segments for, when executed on a computer device, causing the computer device to implement the method of claim 1.

24. A magnetic resonance scanner, comprising:
a recording device to record a first magnetic resonance record and a second magnetic resonance record of an examination object, the first magnetic resonance record and the second magnetic resonance record including an overlap region; and
a processor configured to,
determine a superposed image as weighted superposition of the first magnetic resonance record and the second magnetic resonance record in the overlap region,
transform the first image and the second image on the basis of a comparison of at least one of the first magnetic resonance record and the second magnetic resonance record with the determined superposed image,
determine a further superposed image from the transformed first image and the transformed second image, and
generate an overall image from the further superposed image when at least one convergence criterion is satisfied, wherein
a weighting function which represents a weighting of at least one of the first magnetic resonance record and the second magnetic resonance record at positions of the superposed image is spatially variable in the overlap region and wherein the processor is designed to transform the first magnetic resonance record and the second magnetic resonance record on the basis of a comparison of at least one of the first magnetic resonance record and the second magnetic resonance record with the determined superposed image.

25. A method for combining a first image and a second image of an examination object, the first and second images including an overlap region, the method comprising:
determining whether first pixel values within the overlap region of the first and second images converge with corresponding second pixel values within the overlap region of superposed images by iteratively,
generating, using a weighting function, an associated one of the superposed images as a weighted superposition of both the first and second images such that within the overlap region the weight given to the first pixel values of a respective one of the first and second images decreases in a direction of an edge of the respective one of the first and second images, and
modifying the first pixel values located within the overlap region of the first and second images based on a comparison between the first pixel values of the respective one of the first and second images and the corresponding second pixel values within the associated one of the superposed images; and
designating one of the superposed images as an overall image when the determining determines that, within the overlap region, the corresponding second pixel values of the superposed image converge with the first pixel values.

\* \* \* \* \*